United States Patent [19]

Whipple

[11] Patent Number: 5,312,412
[45] Date of Patent: May 17, 1994

[54] FIXATION ALIGNMENT GUIDE FOR SURGICAL USE

[76] Inventor: Terry L. Whipple, 9009 Norwick Rd., Richmond, Va. 23229

[21] Appl. No.: 12,994

[22] Filed: Feb. 3, 1993

[51] Int. Cl.$^5$ ............................................. A61F 5/00
[52] U.S. Cl. ..................................... 606/96; 606/105
[58] Field of Search ............... 606/57, 87, 96, 102, 606/103, 104, 105

[56] References Cited

U.S. PATENT DOCUMENTS

| | | |
|---|---|---|
| 3,867,932 | 2/1975 | Huene . |
| 4,175,555 | 11/1979 | Herbert . |
| 4,739,751 | 4/1988 | Sapega et al. ............... 606/96 |
| 5,019,079 | 5/1991 | Ross ................................ 606/72 |
| 5,112,335 | 5/1992 | Laboureau et al. ............ 606/88 |
| 5,112,337 | 5/1992 | Paulos et al. .................. 606/96 |
| 5,152,764 | 10/1992 | Goble ............................ 606/96 |
| 5,152,765 | 10/1992 | Ross et al. ..................... 606/99 |
| 5,163,940 | 11/1992 | Bourque ....................... 606/103 |

Primary Examiner—Tamara L. Graysay
Attorney, Agent, or Firm—Richard E. Jenkins

[57] ABSTRACT

An improved device for inserting rigid shafts into opposed segments of a fractured bone including a axially movable shaft having an arm extending outwardly therefrom which is adapted to engage a fractured bone at a first surface location. A tubular guide through which the rigid shaft is inserted is provided which is operatively aligned with the bone engagement arm and includes jaws opposing the bone engagement arm for engaging the fractured bone at a second surface location. The tubular guide is secured to one end of an elongate guide support and the axially movable shaft is adjustably positioned parallel thereto in an aperture extending through the elongate guide support. A securement mechanism is operatively associated with the guide support for securing the axially movable shaft at a desired distance from the jaws of the tubular guide to fixedly engage the fractured bone therebetween.

13 Claims, 7 Drawing Sheets

FIXATION ALIGNMENT GUIDE FOR SURGICAL USE

DESCRIPTION

1. Technical Field

The invention relates to devices particularly adapted for use in orthopaedic surgery, and more specifically to an improved device for joining opposed segments of a fractured bone with a rigid shaft inserted therein.

2. Related Art

As is well known to those familiar with orthopaedic surgical procedures, it is often necessary to secure opposed fractured bone segments together using threaded and/or unthreaded screws and pins. This is a very delicate procedure requiring great surgical skill in order to avoid imposing injury on healthy tissue in proximity to the fractured bone being joined.

Of significance to this type of medical procedure, Dr. Timothy Herbert of Australia developed a unique screw intended primarily for the fixation of fractures of the carpel scaphoid. The screw is the subject matter of U.S. Pat. No. 4,175,555 and comprises threads at opposing ends which are separated by a non-threaded medial segment. The functionality of the screw is provided by the fact that the leading threads define a greater pitch and diameter than the trailing threads of the screw so as to progress through a bone at a higher rate per revolution than the trailing threads and thereby apply a compressive force to opposed segments of a fractured bone. As is also well known to those familiar with orthopaedic surgical procedures, the screw is best inserted by use of an alignment jig developed by Donald R. Huene and the subject matter of U.S. Pat. No. 3,867,932.

The alignment jig disclosed in U.S. Pat. No. 3,867,932 provides an off-set target hook that extends along a small bone and then curves to engage the bone's remote end. A cooperatively associated guide barrel is adapted to slide through the foundation from which the target hook extends to engage the proximal end of the fractured bone, and the guide barrel and target hook can then be locked together to provide compression across the fractured bone. In this fashion, suitable instruments well-known to those skilled in the orthopaedic surgical art are then introduced through the guide barrel including, but not limited to, a twist drill bit, a thread tap, a screw driver and a Herbert Screw. Thus, the Herbert Screw in combination with the Huene alignment jig provide a useful methodology for stabilizing and then transfixing small bone fractures, most notably the carpel scaphoid.

However, the aforementioned system for joining fractured bone segments has certain shortcomings which are well known to those skilled in the art. More specifically, surgical exposure of the carpel scaphoid is usually attained through either a volar or dorsal approach (front or back) and therefore introduction of the Huene guide target hook through the surgical incision necessitated a blind placement of the target hook on the far end of the bone by the surgeon. Furthermore, the introduction of the guide target hook necessitated relatively extensive surgical exposure transecting ligaments that might further destabilize the scaphoid within the wrist or divide its blood supply necessary for fracture healing.

Yet another shortcoming of the prior system using the Herbert Screw and Huene alignment jig was that after inserting the twist drill bit (the first instrument to be passed through the guide barrel and bone) and thereby removing a significant amount of bone, a second adjusted pass was not possible with any assurance of desirable thread purchase in solid bone. In actual practice, many such Herbert Screw placements in clinical practice exit the bone entirely, miss the remote bone fragment, violate the external cortex or articular surface of the bone, or do not achieve satisfactory purchase for rigid fixation. Thus, as can be appreciated, the Huene alignment jig as disclosed in U.S. Pat. No. 3,867,932 suffers inherent shortcomings when actually used in surgical procedures.

Therefore, applicant has developed an improved fixation alignment guide which overcomes the shortcomings of prior art alignment jigs used in joining opposing segments of a fractured bone with screws (including both the Herbert Screw and the Herbert/Whipple Screw disclosed in U.S. Pat. No. 5,019,079), pins, wire and the like while protecting contiguous tissue from damage. More particularly, applicant has developed a fixation alignment guide which is adapted so that one element thereof can be introduced percutaneously under arthroscopic control to engage the distal end of a fractured bone and thereby provide a minimally invasive technique with the attendant reduced surgical exposure, preservation of ligaments, and preservation of clinical blood supply to the bone coursing through the ligaments.

DISCLOSURE OF THE INVENTION

In accordance with the present invention applicant provides a fixation alignment guide for surgical use, particularly for fixation of scaphoid and other small bone fractures. The device comprises an axially movable shaft having an arm extending outwardly therefrom which is adapted to engage a fractured bone at a first surface location. A tubular guide is operatively aligned with the bone engagement arm and has a proximal end and a distal end wherein the proximal end comprises jaw means for engaging the fractured bone at a second surface location substantially opposite the first bone surface location. An elongate guide support is provided for engaging the tubular guide between the proximal and distal ends thereof and further defines an aperture therethrough for movably receiving the axially movable shaft therein. Securement means are operatively associated with the guide support for securing the axially movable shaft at a desired distance from the jaw means of the tubular guide in order to fixedly engage the fractured bone therebetween whereby rigid shafts may be inserted through the tubular guide and implanted into the opposed segments of a fractured bone.

It is therefore the object of the present invention to provide an improved fixation alignment guide for better joining of opposed segments of a fractured bone by means of insertion of a rigid shaft into opposing segments thereof.

It is another object of the present invention to provide an improved fixation alignment guide for joining opposed segments of a fractured bone which in use minimizes necessary surgical exposure by allowing the axially movable shaft portion thereof to be introduced percutaneously under arthroscopic control so as to engage the far end of a fractured bone.

It is still another object of the present invention to provide an improved fixation alignment guide which is adapted for insertion of a primary guide wire through the bone and the correct position thereof confirmed radiographically, and the insertion of one or more accessory guide wires through the bone to control rotation of the device and/or to provide additional stabilization of bone fragments during subsequent surgical procedures performed therewith.

Some of the objects of the invention having been stated other objects will become evident as the description proceeds, when taken in connection with the accompanying drawings described hereinbelow.

BEST MODE FOR CARRYING OUT THE INVENTION

Figure 1:
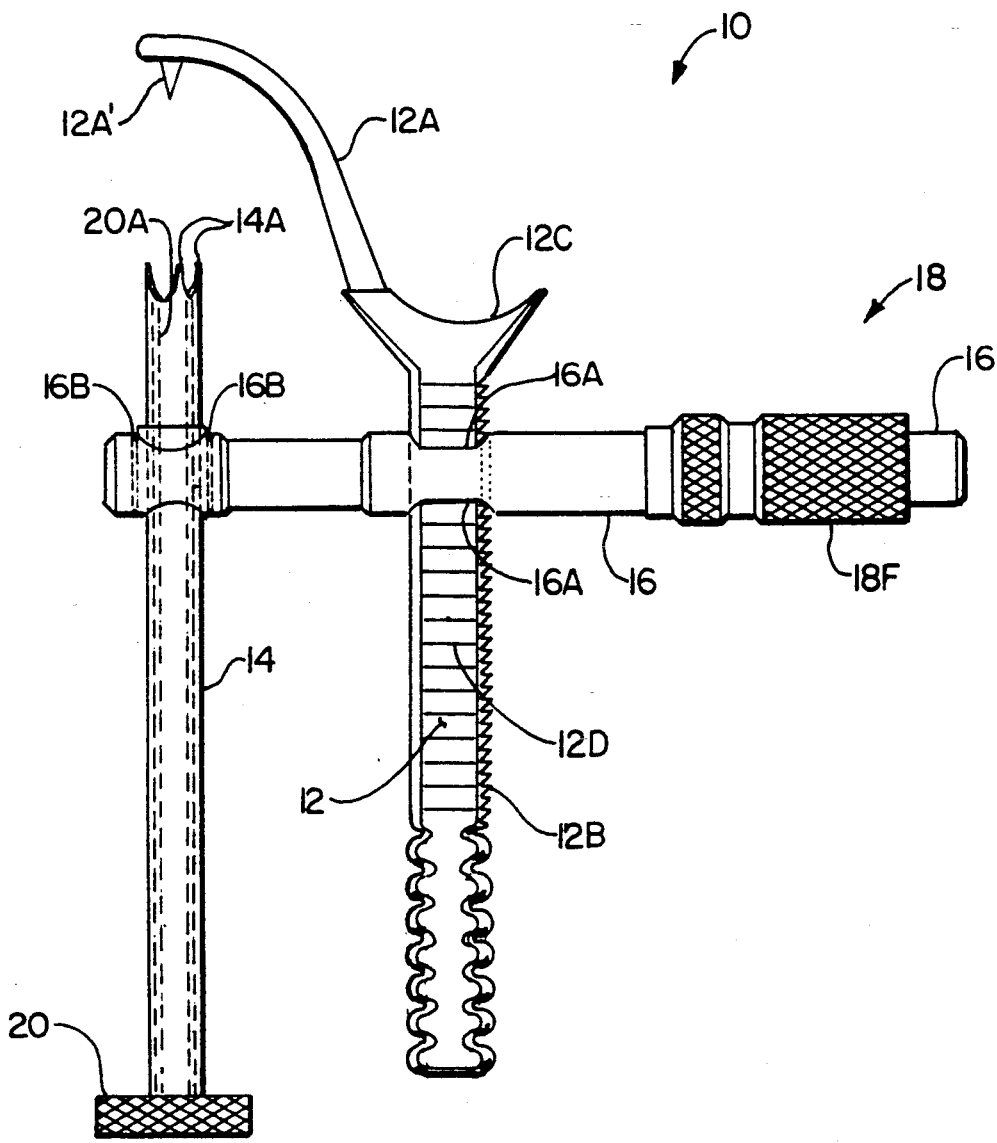
FIG. 1 is an side elevation view of a fixation alignment guide embodying the principles of the instant invention.
Figure 2:
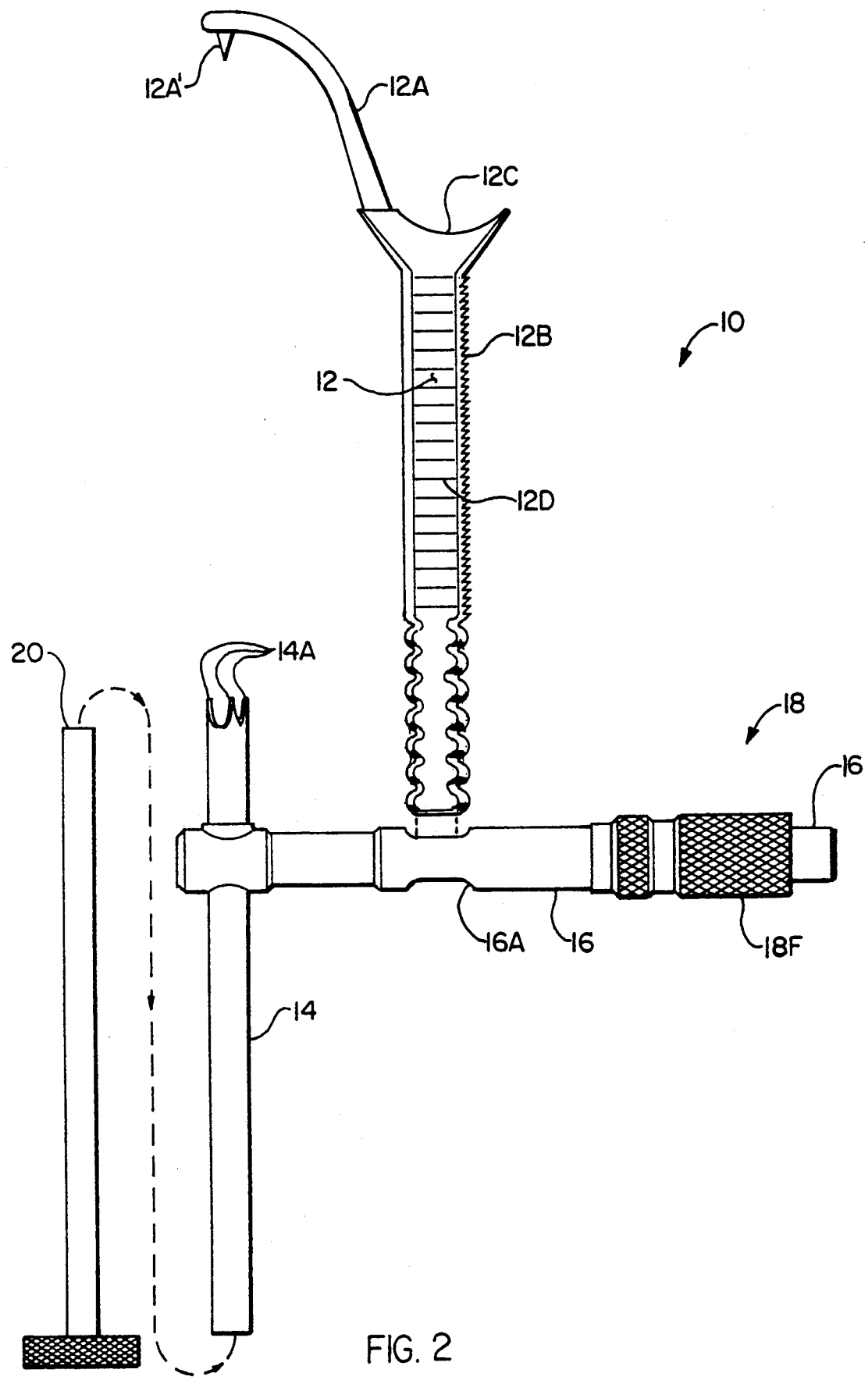
FIG. 2 is an exploded side elevation view of the fixation alignment guide shown in FIG. 1.
Figure 3:
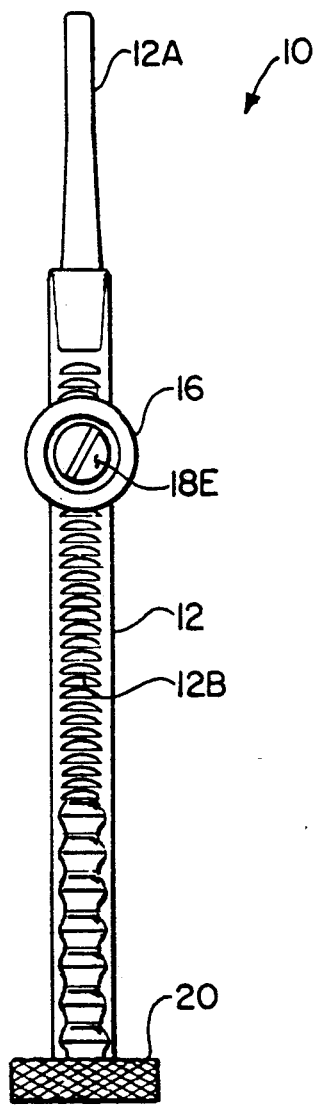
FIG. 3 is an end elevation view of the fixation alignment guide shown in FIG. 1.

Referring now more specifically to FIGS. 1-6 of the drawings wherein like references designate like or corresponding parts in each of the figures, there is shown in FIG. 1 the fixation alignment guide of the invention which is generally designated 10. However, applicant wishes to observe that although the preferred embodiment of the invention is shown and described herein, it is recognized that various details of the invention may be changed without departing from the scope of the invention, and the scope of the invention is not intended to be limited in any fashion whatsoever to the illustrative details and preferred embodiment disclosed herein.

Fixation alignment guide 10 is a novel assembly formed of an axially movable shaft 12, a tubular guide 14, and elongate guide support 16 for fixedly engaging tubular guide 14 at one end thereof and provided with an aperture 16A in the medial portion thereof for slidably receiving axially movable shaft 12 therein. A ratchet mechanism 18 (see particularly FIGS. 5A and 5B) is carried by elongate guide support 16 which serves to selectively engage and disengage axially movable shaft 12 in a fashion which will be explained in specific detail hereinbelow. Optionally, at least one bushing 20 is provided which has a passageway 20A extending therethrough and which is adapted to be inserted into tubular guide 14 as desired to reduce its internal diameter to allow for the precise insertion of primary guide wires (not shown) or the like through tubular guide 14 during use of fixation alignment guide 10 to insert a rigid shaft into opposed segments of a fractured bone, particularly scaphoid and other small bones which lend themselves to use of the device of the invention.

Referring now particularly to FIGS. 1-4, axially movable shaft 12 is formed from an elongate shaft element having an arm 12A extending outwardly therefrom with a pin element 12A' depending downwardly therefrom for engaging a fractured bone at a first location at the far end of the bone. Axially movable shaft 12 further includes ratchet teeth 12B along a portion of the length of the backside thereof for engagement with ratchet mechanism 18 carried by elongate guide support 16 in a cooperative manner which will be explained in detail below but, for general purposes, can be understood to allow slidable movement of shaft 12 inwardly when finger recess 12C is depressed inwardly toward elongate guide support 16, but to lock when a force is applied to shaft 12 in the opposite direction.

Referring now more specifically to tubular guide 14, it can be appreciated that the tubular guide terminates in a plurality of teeth or tines 14A to facilitate engagement of the fractured bone at a second bone surface location substantially opposite the engagement at the first surface location by pin 12A' of arm 12A of axially movable shaft 12. Tines 14A may be of any suitable size and number to provide a stable fixation at the second surface engagement location of a fractured bone.

At this part of the description, it should also be noted that the distance defined between pin 12A' and tines 14A (or the first and second bone engagement surfaces) can be determined by a suitable scale 12D provided on each side of axially movable shaft 12. Scale 12D eliminates the need for measuring the aforementioned critical distance in another way and provides the data necessary for exact and safe adjustment of device 10 in view of the length of the rigid shaft to be inserted. In this regard, although device 10 is particularly adapted for insertion of the Herbert Screw and Herbert/Whipple Screw, fixation alignment guide 10 will also accommodate other rigid shafts including, but not limited to, molly-bolt devices, barbed nails, bone grafts, bone dowels and other similar elements. The measurement of the distance between tines 14A of tubular guide 14 and pin 12A' of axially movable shaft 12 is determined, most suitably, by merely reading the number inscribed on scale 12D at the juncture of scale 12D and aperture 16A of elongate guide support 16 (see, for example, FIG. 1).

Figure 5A:
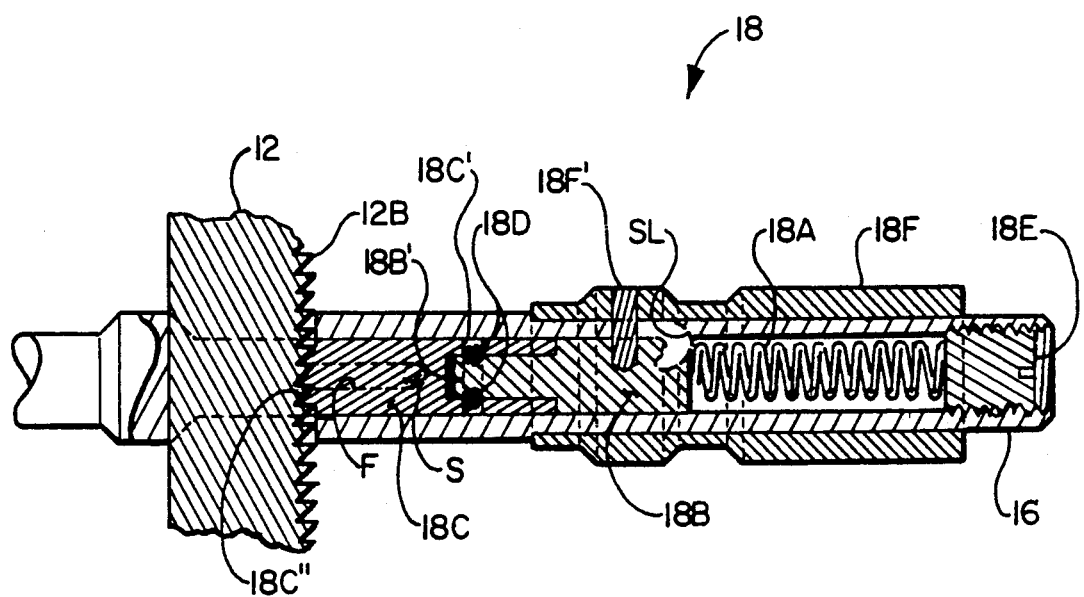
FIGS. 5A and 5B are vertical cross sectional views of the ratchet mechanism of the fixation alignment guide shown in FIG. 1 in the locked and released positions, respectively.
Figure 5B:
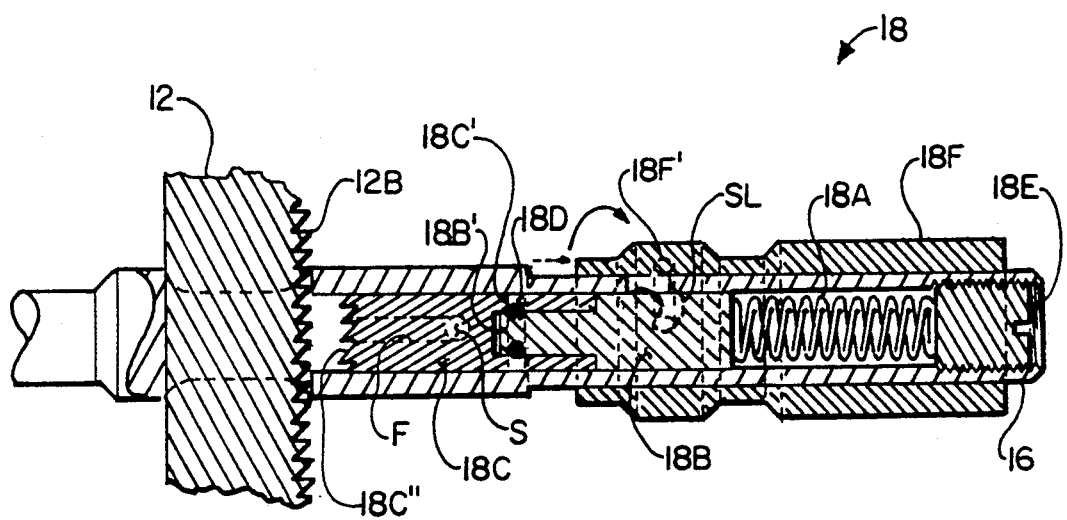
Figure 6:
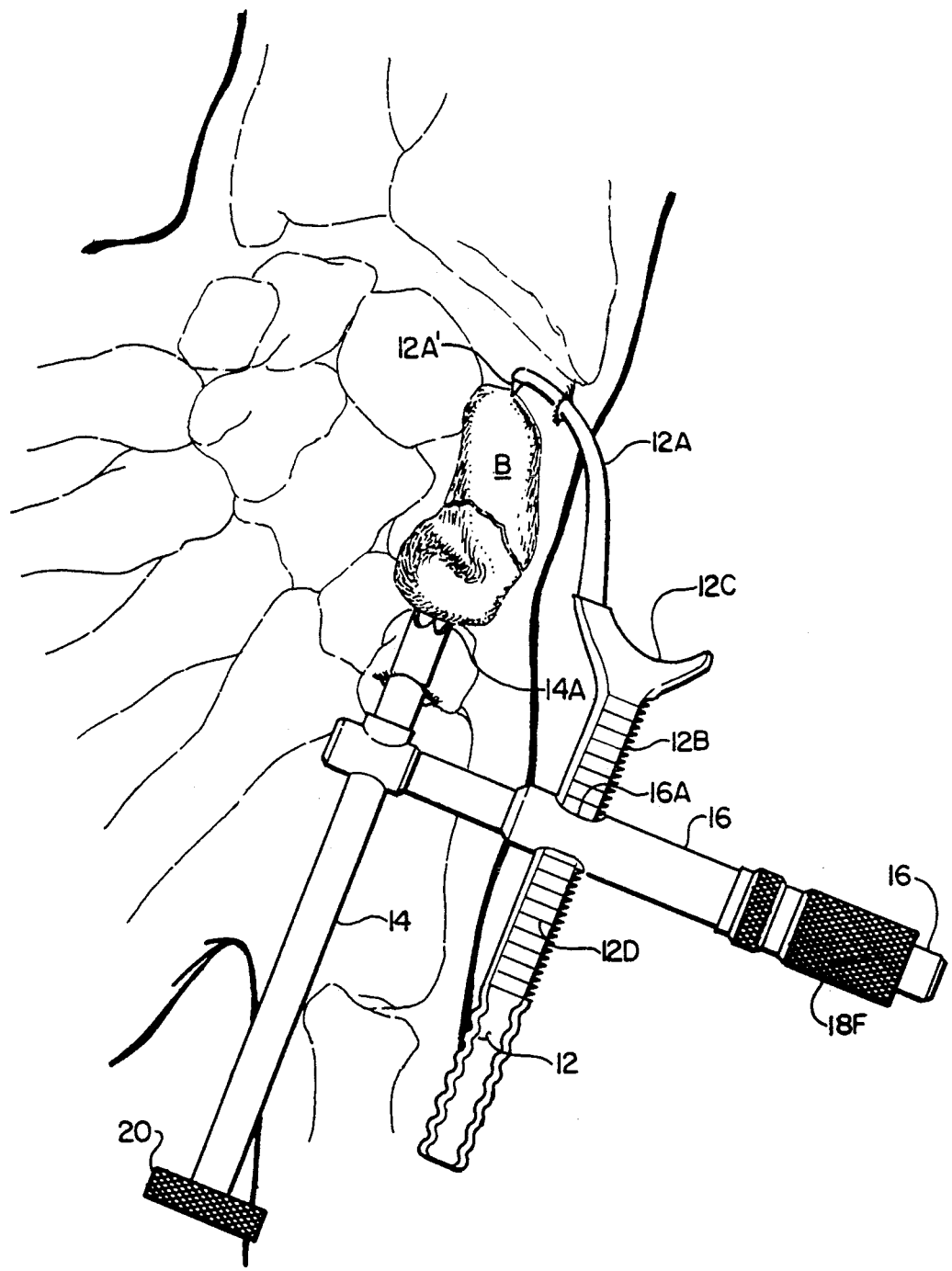
FIG. 6 is an environmental view showing the fixation alignment guide of FIG. 1 employed so as to be engaging a fractured scaphoid bone in the wrist of a patient.

Finally, for an understanding of the structure and functionality of ratchet mechanism 18, reference should now be made to FIGS. 5A and 5B. Ratchet mechanism 18 essentially comprises spring 18A which is normally urged against a ratchet engagement and disengagement assembly consisting of pivot shaft 18B which is adapted for both axial and rotational movement and which engages ratchet pin 18C which is adapted exclusively for axial movement. Pivot shaft 18B and ratchet pin 18C are cooperatively engaged by bearings 18D which reside within radial groove 18B' of pivot shaft 18B and corresponding radially extending apertures 18C' within ratchet pin 18C. In this fashion, spring 18A urges pivot shaft 18B and ratchet pin 18C inwardly wherein ratchet teeth 18C" of ratchet pin 18C engage ratchet teeth 12B of axially movable shaft 12. Thus, whereas pivot shaft 18B is adapted to move both axially and rotationally inwardly ratchet pin 18C can only move axially inwardly by virtue of flat portion F provided on one side thereof and against which set screw S is locked down (and sealed) into a position which allows slidable movement of ratchet pin 18C but which prevents any significant degree of rotational movement in either direction. This is necessary to assure that ratchet teeth 18C" are always properly oriented to register with the ratchet teeth 12B (or blade) of axially movable shaft 12. Also, a set screw 18E is provided at the remote end of spring 18A and within elongate guide support 16 in order to adjust the tension of spring 18A to a desired level for proper functioning of alignment guide 10.

Still referring to FIGS. 5A and 5B and ratchet mechanism 18, it can be appreciated that as axially movable shaft 12 is urged toward elongate guide support 16 it will advance due to slidable movement of ratchet teeth 12B of shaft 12 over ratchet teeth 18C" of ratchet pin 18C, but movement in the opposite direction is prevented by the flat edges of engaged ratchet teeth 12B and 18C". However, axially movable shaft 12 may be released for movement in the aforesaid opposite direction by merely simultaneously rotating and pulling upon sleeve 18F in the direction of set screw 18E which serves to disengage ratchet teeth 18C" of ratchet pin 18C from ratchet teeth 12B of movable shaft 12.

This is accomplished since sleeve 18F includes an inwardly extending rigid pin 18F, which slides within an arcuate slot SL defined within elongate guide support 16 and terminates in fixed engagement with pivot shaft 18B. In this fashion, when sleeve 18F is pulled outwardly and rotated it serves to pull pin 18F' through an arcuate pathway which thereby serves to both rotate and axially withdraw fixedly connected pivot shaft 18B outwardly toward the end of elongate guide support 16 in which set screw 18E resides. Pivot shaft 18B in turn axially withdraws ratchet pin 18C toward the outside end of elongate guide support 16 so as to release ratchet teeth 18C" from engagement with ratchet teeth 12B of movable shaft 12. When sleeve 18F has been fully rotated and pulled toward the outer end of elongate guide support 16 (see FIG. 5B) it serves to lock pivot shaft 18B and ratchet pin 18C into the withdrawn or released position by virtue of pin 18F' which is affixed to pivot shaft 18B at one end and sleeve 18F at the other. The process is merely reversed in order to change alignment guide 10 from the unlocked (FIG. 5A) to the locked (FIG. 5B) mode whereby movement of shaft 12 will be permitted in one direction but stopped in the other.

In this fashion, the ratchet mechanism 18 of fixation alignment guide 10 can be seen to allow one-handed locking and unlocking by a physician and/or to allow the physician to keep device 10 in an unlocked position until the locked position is desired.

Figure 4:
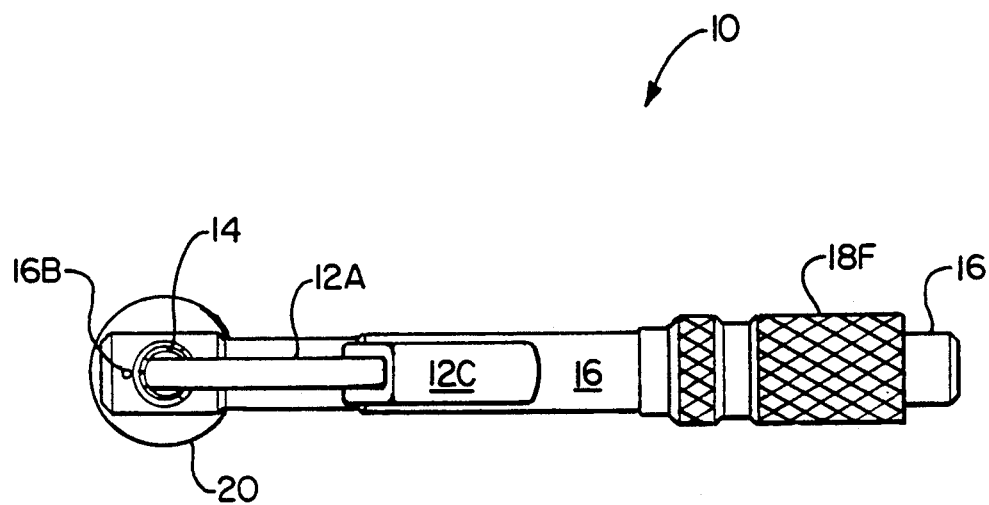
FIG. 4 is a top plan view of the fixation alignment guide shown in FIG. 1.

Finally, with reference particularly to FIG. 1 and 4 of the drawings, it can be appreciated that elongate guide support 16 of alignment guide 10 provides for two parallel passageways or cannulations adjacent tubular guide 14 in elongate guide support 16. The cannulations, designated 16B, are intended to provide a passageway for the fixation of accessory wires into the fractured bone to stabilize bone fragments and provide rotational control of bone fragments during the drilling and rigid shaft insert steps required in surgical use of alignment guide 10.

OPERATION OF FIXATION ALIGNMENT GUIDE

Applicant believes that one skilled in the art would fully understand use of device 10 from the foregoing detailed description. However, applicant desires to describe briefly a representative surgical procedure utilizing the device of the invention. It will be appreciated, of course, by those skilled in the art that many other procedures can be performed with device 10 and the procedure to be described hereinbelow is merely intended to be representative and in no manner to limit the scope of potential uses of the invention.

The arthroscopic procedure for use of alignment guide 10 to address the scaphoid fracture of bone B (see particularly FIG. 6) would entail the following recommended procedural steps.

Preparation

Use either regional or general anesthesia. Apply a tourniquet, and prepare and drape the limb in the standard fashion. The use of an arm extension table and a traction tower, or similar traction arrangement, is recommended.

Exposure

Make a 12 to 15 mm incision, centered over the volar tubercle of the trapezium just radial to the flexor carpi radialis tendon. Identify and open the scaphotrapezial joint through a transverse capsulotomy. Make a T-shaped incision in the capsule and periosteum over the trapezium, meeting the transverse capsulotomy. Turn the capsular flaps distally by subperiosteal dissection.

Excise the volar tubercle on the trapezium with a 3/16 inch osteotome. Remove enough of the tubercle to expose a portion of the distal pole of the scaphoid when the first metacarpal is hyperextended. Place a small self-retaining retractor in the incision. Position the forearm vertically in the traction tower with 10 pounds of axial traction applied to the index and long fingers.

Fracture Reduction

Gently introduce the arthroscope through the radial midcarpal (RMC) portal. To avoid applying excessive pressure during insertion of the arthroscope sheath and trocar, spread the subcutaneous tissue and lance the capsule with a No. 11 scalpel. Briefly flush the joint.

Insert an inflow cannula in the ulnar midcarpal (UMC) portal. Be sure it will not interfere with instrumentation. Clear the hemarthrosis, if present, and examine the fracture line for any evidence of displacement or angulation. If the degree of angulation or displacement is small, reduce the fracture by placing the wrist in extension or supination. This should reverse the humpback deformity and close the fracture line. If the fracture line remains open, inset a 0.045 inch K-wire percutaneously into the scaphoid tubercle volarly and into the proximal pole dorsally. Use these wires to manipulate the fracture fragments. Confirm the reduction using a radiograph or fluoroscope.

Surgical Procedure

Step 1—Insert Alignment Guide

Transfer the arthroscope to the 3-4 portal and move the inflow cannula to the arthroscopy sheath or the 6-U portal. Establish a 1-2 portal and dilate it to admit the axially movable shaft 12 and arm 12A of the alignment guide.

Advance shaft 12 and arm 12A under arthroscopic control between the radius and scaphoid to the appropriate target point on the proximal pole of the scaphoid. This point should be approximately 1-2 mm from the scapholunate ligament along the dorsal aspect of the proximal pole. Rotate shaft 12 and arm 12A so its angle accommodates the convex contour of the scaphoid and embed pin element 12A' of arm 12A into the articular cartilage at the target point. Use slight traction to hold it in place while tubular guide 14 and elongate guide support 16 is attached.

Hyperextend the thumb to displace the trapezium dorsally on the distal articular surface of the scaphoid.

Swing tubular guide 14 of alignment guide 10 into position on the radial aspect of the distal pole of the scaphoid. Squeeze movable shaft 12 toward tubular guide 14 to push the tines 14A of the tubular guide onto the bone.

When the alignment guide 10 has been applied, check its alignment visually to ensure that the screw to be inserted will lie in the optimum position. Also check the reduction of the fracture and make any necessary adjustments. If an adjustment is necessary compression can be released by pulling sleeve 18F of ratchet mechanism 18 on alignment guide 10.

Step 2—Determine Screw Length

Read the screw length from scale 12D of movable shaft 12 for the calibrations of the guide.

Step 3—Insert Wires

Insert a free-hand guide insert sleeve or bushing 20 into tubular guide 14 of the alignment guide. Wire penetration can be controlled using a flat depth gauge to inset the primary guide wire into a wire driver at the correct length. Drive the wire into the bone through the insert sleeve until the wire driver bottoms out on the sleeve. Then remove the wire driver and sleeve.

Use an x-ray or image intensifier to verify the positioning of the primary guide wire. There should be at least 2.0 mm of bone on both sides of the wire in every projection. If necessary withdraw the wire, reposition the alignment guide, and reinsert the wire.

Use a depth gauge to insert the accessory guide wire into a wire driver at the correct depth. Place this wire parallel to the primary wire through one of two cannulations 16B adjacent to tubular guide 14 of alignment guide 10. This will help prevent fragment rotation during screw insertion. Drive the wire until the wire driver bottoms out on the end of tubular guide 14. Then bend the accessory wire away from tubular guide 14 to remove it from the path of the instruments.

Step 4—Broach the Cortex

For thin cortex, or osteoporotic bone, this step is not necessary. For hard bone, attach a cannulated cortical broach to a modular handle and slide it over the primary guide wire. Turn the handle clockwise and advance the broach until it bottoms out on the end of tubular guide 14. This will remove a small amount of bone from the cortical surface and facilitate further instrumentation. Alternatively, power instruments can be used to drive this broach.

Step 5—Drill

Use a cannulated step drill over the primary guide wire to drill the pilot hole. Slide an adjustable stop sleeve onto the drill and set it for the appropriate screw length. The hole should be drilled using a cannulated Jacob's check and power drill. Alternatively, for soft bone, the cannulated step drill can be attached to the modular handle for manual drilling. The small diameter of this drill is for the leading threads of the screw while the larger diameter is for the trailing threads and shank. Drill until the sleeve bottoms out on the end of tubular guide 14.

Step 6—Tap

For sclerotic bone only, attach a cannulated tap to the modular handle. Slide the adjustable stop sleeve onto the tap and set it for the appropriate screw length. Tap the hole for the leading threads of the screw. This is an optional step recommended for sclerotic bone because the leading and trailing threads of the screw implant are self-tapping. Tap until the sleeve bottoms out on the end of tubular guide 14. The tap must not be turned beyond the depth of the sleeve or the bone threads will be stripped.

Step 7—Insert the Screw

Attach a cannulated screwdriver to the modular handle. Insert the screw and screwdriver over the guide wire and into tubular guide 14 of alignment guide 10. Turn the screwdriver until the stop bottoms out on the end of tubular guide 14. The screwdriver should be advanced a few more times to further bury the screw head below the bone surface.

When the screw is fully seated, remove the cannulated screwdriver, the primary guide wire, and the alignment guide. The accessory guide wire can also be removed or, if desired, it can be left in place for the first two weeks to help control rotation of the bone fragments during initial healing. To ensure that the screw head is completely buried, inspect the entry point on the distal pole of the scaphoid. If necessary, reapply the screwdriver and rotate the screw one more revolution.

Finally, put the wrist joint through a full range of movements to check the security of fixation and to ensure that the screw has not penetrated proximally. This can also be checked by reinserting the arthroscope in the 3-4 portal. Carefully trim off any protuberant bone graft.

It will be understood that various details of the invention may be changed without departing from the scope of the invention. Furthermore, the foregoing description is for the purpose of illustration only, and not for the purpose of limitation—the invention being defined by the claims.

I claim:

1. A device for inserting rigid shafts into opposed segments of a fractured bone the device comprising:
    an axially movable shaft having an arm extending outwardly therefrom said arm being adapted to engage a fractured bone at a first surface location;
    a tubular guide operatively aligned with said bone engagement arm and having a proximal end and a distal end wherein said proximal end comprises means for engaging the fractured bone at a second surface location substantially opposite said first bone surface location;
    an elongated guide support for engaging said tubular guide between the proximal and distal ends of said tubular guide and defining an aperture therethrough for adjustably receiving said axially movable shaft therein; and
    securement means operatively associated with said guide support for securing said axially movable shaft at a desired distance from said engagement means of said tubular guide in order to fixedly engage the fractured bone therebetween;
    whereby rigid shafts may be inserted through said tubular guide and implanted into opposed segments of the fractured bone, and
    wherein said elongate guide support includes one or more apertures therethrough located adjacent and parallel to said tubular guide, said apertures defining a smaller diameter passageway than said tubular guide and allowing for selective insertion of guide wires into the fractured bone.

2. A device for inserting rigid shafts into opposed segments of a fractured bone the device comprising:
    an axially movable shaft having an arm extending outwardly therefrom, said are being adapted to engage a fractured bone at a first surface location;

a tubular guide operatively aligned with said bone engagement arm and having a proximal end and a distal end wherein said proximal end comprises means for engaging the fractured bone at a second surface location substantially opposite said first bone surface location;

an elongate guide support for engaging said tubular guide between the proximal and distal ends of said tubular guide and defining an aperture therethrough for adjustably receiving said axially movable shaft therein; and securement means operatively associated with said guide support for securing said axially movable shaft at a desired distance from said engagement means of said tubular guide in order to fixedly engage the fractured bone therebetween;

whereby rigid shafts may be inserted through said tubular guide and implanted into opposed segments of the fractured bond, and wherein said securement means comprises:
 a. ratchet teeth provided along at least a portion of the length of said axially movable shaft;
 b. a ratchet pin carried by said elongate guide support and said ratchet pin to cooperatively engage said ratchet teeth of said axially movable shaft so as to allow said shaft to be slidably movable relative thereto in one direction and to lockingly engage said shaft so as to prevent slidable movement of said shaft in the other direction;
 c. a sleeve rotatably mounted to said elongate guide support in spaced apart relationship to said axially movable shaft; and
 d. connector means operatively connecting said sleeve to said ratchet pin and adapted to withdraw said ratchet pin from cooperative engagement with said ratchet teeth of said axially movable shaft when said sleeve is rotatably actuated and thereby release said axially movable shaft for slidable movement in said one direction and said other direction.

3. A device for inserting rigid shafts into opposed segments of a fractured bone the device comprising:

an axially movable shaft having an arm extending outwardly therefrom, said arm being adapted to engage a fractured bone at a first surface location;

a tubular guide operatively aligned with said bone engagement arm and having a proximal end and a distal end wherein said proximal end comprises means for engaging the fractured bone at a second surface location substantially opposite said first bone surface location;

an elongate guide support for engaging said tubular guide between the proximal and distal ends of said tubular guide and defining an aperture therethrough for adjustably receiving said axially movable shaft therein; and securement means operatively associated with said guide support for securing said axially movable shaft at a desired distance from said engagement means of said tubular guide in order to fixedly engage the fractured bone therebetween;

whereby rigid shafts may be inserted through said tubular guide and implanted into opposed segments of the fractured bone, and wherein a bushing defining an aperture therethrough is provided which is inserted into said tubular guide to provide a reduced diameter passageway through said tubular guide for insertion of a guide wire into the fractured bone.

4. A device for inserting rigid shafts into opposed segments of a fractured bone, the device comprising;

an axially movable shaft having an arm extending outwardly therefrom, said arm being adapted to engage a fractured bone at a first surface location and said arm having a base;

a tubular guide operatively aligned with said bone engagement arm and having a proximal end and a distal end wherein said proximal end comprises jaw means for engaging the fractured bone at a second surface location substantially opposite said first bone surface location;

an elongate guide support for engaging said tubular guide between the proximal and distal ends of said tubular guide and defining an aperture therethrough for slidably receiving said axially movable shaft therein; and securement means operatively associated with said guide support for securing said axially movable shaft at a desired distance from said jaw means of said tubular guide in order to fixedly engage the fractured bone therebetween, said securement means comprising: (1) ratchet teeth provided along at least a portion of the length of said axially movable shaft; (2) a ratchet pin carried by said elongate guide support and said ratchet pin to cooperatively engage said ratchet teeth of said axially movable shaft so as to allow said shaft to be slidably movable relative thereto in one direction and to lockingly engage said shaft so as to prevent slidable movement of said shaft in the other direction; (3) a sleeve rotatably mounted to said elongate guide support in spaced apart relationship to said axially movable shaft; and (4) connector means operatively connecting said sleeve to said ratchet pin and adapted to withdraw said ratchet pin from cooperative engagement with said ratchet teeth of said axially movable shaft when said sleeve is rotatably actuated and thereby release said axially movable shaft for slidable movement in said one direction and said other direction;

whereby rigid shafts may be inserted through said tubular guide and implanted into opposed segments of the fractured bone.

5. A device according to claim 4 wherein said arm of said axially movable shaft includes a pin element for engagement of the bone depending downwardly from the free end thereof and substantially axially aligned with said tubular guide.

6. A device according to claim 4 wherein said axially movable shaft includes measuring means for indicating the distance between said first bone surface location engaged by said arm thereof and said second bone surface engaged by said jaw means of said tubular guide.

7. A device according to claim 6 wherein said measuring means is a scale inscribed on said axially movable shaft.

8. A device according to claim 4 wherein said axially movable shaft includes an arcuate finger receiving portion at the base of said arm to facilitate slidably urging said shaft towards said elongate guide support.

9. A device according to claim 4 wherein said axially movable shaft extends substantially pendicularly in relationship to said elongate guide support and substantially parallel to said tubular guide.

10. A device according to claim 4 wherein said jaw means of said tubular guide comprises a plurality of tines extending generally outwardly from said proximal end of said tubular guide and parallel to a longitudinal axis thereof.

11. A device according to claim 4 wherein said elongate guide support fixedly engages said tubular guide adjacent one end thereof, slidably receives said axially movable shaft substantially in the medial portion thereof, and carries said securement means between the other end thereof and said axially movable shaft.

12. A device according to claim 12 wherein said elongate guide support includes one or more apertures therethrough located adjacent and parallel to said tubular guide, said apertures defining a smaller diameter passageway than said tubular guide and allowing for selective insertion of guide wires into the fractured bone.

13. A device according to claim 4 wherein a bushing defining an aperture therethrough is provided which is inserted into said tubular guide to provide a reduced diameter passageway through said tubular guide for insertion of a guide wire into the fractured bone.

* * * * *